US009572795B2

(12) United States Patent
Hossainy et al.

(10) Patent No.: US 9,572,795 B2
(45) Date of Patent: Feb. 21, 2017

(54) DRUG DELIVERY SYSTEM AND METHOD OF TREATMENT OF VASCULAR DISEASES USING PHOTODYNAMIC THERAPY

(75) Inventors: Syed Hossainy, Hayward, CA (US);
Dariush Davalian, San Jose, CA (US);
Mikael Trollsas, San Jose, CA (US);
John Stankus, Campbell, CA (US);
Yuet Mei Khong, Sunnyvale, CA (US);
Jinping Wan, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 610 days.

(21) Appl. No.: 13/572,507

(22) Filed: Aug. 10, 2012
(Under 37 CFR 1.47)

(65) Prior Publication Data
US 2012/0310142 A1   Dec. 6, 2012

Related U.S. Application Data (63) Continuation of application No. 12/491,063, filed on Jun. 24, 2009, now abandoned.

(51) Int. Cl.

| | | |
|---|---|---|
| *A61M 37/00* | (2006.01) | |
| *A61K 31/409* | (2006.01) | |
| *A61K 9/00* | (2006.01) | |
| *A61K 9/127* | (2006.01) | |
| *A61K 9/51* | (2006.01) | |
| *A61L 29/16* | (2006.01) | |
| *A61K 41/00* | (2006.01) | |
| *A61M 25/00* | (2006.01) | |
| *A61M 25/10* | (2013.01) | |

(52) U.S. Cl.
CPC ........... *A61K 31/409* (2013.01); *A61K 9/0009* (2013.01); *A61K 9/0019* (2013.01); *A61K 9/1272* (2013.01); *A61K 9/5146* (2013.01); *A61K 41/0071* (2013.01); *A61L 29/16* (2013.01); *A61L 2300/224* (2013.01); *A61L 2300/626* (2013.01); *A61M 25/0045* (2013.01); *A61M 25/10* (2013.01); *A61M 2025/105* (2013.01); *A61M 2025/1086* (2013.01)

(58) Field of Classification Search
CPC .. A61K 31/409; A61K 9/0009; A61K 9/0019; A61K 9/1272; A61K 9/5146; A61K 41/0071; A61L 29/16; A61L 2300/224; A61L 2300/626; A61M 25/0045; A61M 25/10; A61M 2025/105; A61M 2025/1086
See application file for complete search history.

(56) References Cited

U.S. PATENT DOCUMENTS

| | | | |
|---|---|---|---|
| 5,214,036 A | 5/1993 | Allison et al. | |
| 5,429,634 A | 7/1995 | Narciso, Jr. | |
| 5,885,613 A | 3/1999 | Holland et al. | |
| 6,054,449 A * | 4/2000 | Robinson et al. | 514/185 |
| 6,171,577 B1 * | 1/2001 | Kasina et al. | 424/1.69 |
| 6,730,735 B2 | 5/2004 | Davis et al. | |
| 7,008,411 B1 | 3/2006 | Mandrusov et al. | |
| 7,189,562 B2 | 3/2007 | Lewis et al. | |
| 2001/0005501 A1 | 6/2001 | Marriott et al. | |
| 2005/0031541 A1 * | 2/2005 | Gierskcky et al. | 424/9.6 |
| 2006/0165744 A1 | 7/2006 | Jamil et al. | |
| 2007/0092558 A1 * | 4/2007 | Heavner et al. | 424/450 |
| 2008/0081075 A1 | 4/2008 | Hsiue et al. | |
| 2008/0146489 A1 | 6/2008 | Pacetti et al. | |
| 2009/0047318 A1 | 2/2009 | Ludwig et al. | |
| 2009/0148491 A1 | 6/2009 | Hossainy et al. | |
| 2009/0156982 A1 | 6/2009 | Petrie et al. | |
| 2010/0331819 A1 | 12/2010 | Hossainy et al. | |

FOREIGN PATENT DOCUMENTS

| | | | | |
|---|---|---|---|---|
| WO | WO2007/109364 | * | 9/2007 | ............... C12Q 1/68 |
| WO | WO 2007/109364 | | 9/2007 | |

OTHER PUBLICATIONS

John Spikes & Giulio Jori, Photodynamic Therapy of Tumors and Other Diseases Using Porphyrins, 2 Lasers Med. Sci. 3 (1987).*
Aruna Roby, et al, Solubilization of Poorly Soluble PDT Agent, Meso-tetraphenylporphin, in Plain or Immunotargeted PEG-PE Micelles Results in Dramatically Improved Cancer Cell Killing In Vitro, 62 Eur. J Pharma. Biopharma. 235 (2006).*
Luis Guzman, et al, Local Intraluminal Infusion of Biodegradable Polymeric Nanoparticles; A Novel Approach for Prolonged Drug Delivery after Balloon Angioplasty, 94 Circulation 1441 (1996).*
Antimisialris et al., Journal of Liposome Research, 16: pp. 303-309 (2006).
Aruna Roby et al., "Solubilization of Poorly Soluble PDT Agent, Meso-tetraphenylporphin, in Plain or Immunotargeted PEG-PE Micelles Results in Dramatically Improved Cancer Cell Killing In Vitro", 62 Eur. J Pharma. Biopharma, 235 (2006).
Castro et al., "Development of a new solid lipid nanoparticle formulation containing retinoic acid for topical treatment of acne", J. of Microencapsulation 24, pp. 395-407 (2007).
Grabovac et al., "Development and In Vitro Evalucation of Surface Modified Poly(lactide7co-glycolid) Nanoparticles with Chitosan-4-thiobutylamide", Drug development and Industrial Pharmacey, 33: pp. 767-774 (2007).
Kast et al., Biomaterials 22, pp. 2345-2352 (2001).
Kim et al., "Polymeric worm micelles as nano-carriers for drug delivery", Nanotechnology 16, pp. 484-491 (2005).
Kurnar, "Preparation and Characterization of cationic PLGA nanospheres as DNA carriers", Biomaterials 25, pp. 1771-1777 (2004).
Lai et al., "Rapid transport of large polymeric nanoparticles in fresh undiluted human mucus", PNAS vol. 104, No. 5, pp. 1482-1487 (2007).

(Continued)

*Primary Examiner* — Sean Basquill
(74) *Attorney, Agent, or Firm* — Squire Patton Boggs (US) LLP (57) ABSTRACT

This invention relates to photodynamic therapy (PDT) of vulnerable plaque using two pluralities of nanoparticles, one plurality comprising a PDT agent that is sensitive to blue-green light wherein the nanoparticles are capable of penetrating only into the fibrous cap of the vulnerable plaque and one plurality comprising a PDT agent that is sensitive to red light wherein the nanoparticles are capable of penetrating into the core of the vulnerable plaque.

17 Claims, 1 Drawing Sheet

(56) References Cited

OTHER PUBLICATIONS

Lee "Thiolated chitosan Nanoparticles enhance anti-inflammaotyr effects of intranasally delivered thiophylline", Respiratory Research, 7:112, pp. 1-10 (2006).
Lorenceau et al., "Generation of Polymerosomes from Double-Emulsions", Langmuir 21, pp. 9183-9186 (2005).
Mann et al., "Cell adhesion peptides alter smooth muscle cell adhesion, proliferation, migration, and matrix protein synthesis on modified surfaces and in polymer scaffolds", John Willey & Sons, Inc. pp. 86-93 (2002).
Pautot et al., "Production of Unilamellar Vesicles Using an Inverted Emulsion", Langmuir 19, pp. 2870-2879 (2003).
Raz et al., "Reduced negative surface charge on arterial endothelium of diabetic rat", Diabetologia 31, pp. 618-620 (1988).
Wilhelm et al., "Intracellular uptake of anionic superparamagnetic nanoparticles as a function of their surface coating", Biomaterials 24, pp. 1001-1011 (2003).
Yan et al., "BLIMP1 regulates cell growth through repression of p53 transcription", PNAS vol. 104, No. 6, pp. 1841-1846 (2007).
Zahr et al., "Macrophage Uptake of Core-Shell Nanoparticles Surface Modified with Poly(ethylene glycol)", Longmuir 22, pp. 8178-8185 (2006).

* cited by examiner

DRUG DELIVERY SYSTEM AND METHOD OF TREATMENT OF VASCULAR DISEASES USING PHOTODYNAMIC THERAPY

RELATED APPLICATIONS

This application is a continuation of application Ser. No. 12/491,063 filed on 24 Jun. 2009, which application is incorporated herein as if fully set forth herein.

FIELD OF INVENTION

This invention relates to local or regional delivery of a photodynamic therapy drug for the treatment of vascular diseases.

BACKGROUND

Photodynamic therapy (PDT) has been used primarily for the treatment of cancer. It is believed that, given a suitable delivery vehicle and method, PDT drugs, either alone or in combination with other drugs, should find utility in the treatment of vascular diseases. This invention provides such a delivery vehicle and method.

SUMMARY OF THE INVENTION

Thus, in one aspect, this invention relates to a method of treating vulnerable plaque in a patient in need thereof, comprising:
administering to the site of a vulnerable plaque, having a fibrous cap and an interior core, a first plurality of nanoparticles comprising a first PDT drug having an excitation wavelength in the blue-green region of the electromagnetic spectrum wherein the first plurality of nanoparticles either affix to the surface of the fibrous cap or penetrate only into the fibrous cap;
concurrently administering to the site of the vulnerable plaque a second plurality of nanoparticles comprising a second PDT drug having an excitation wavelength in the red region of the electromagnetic spectrum wherein the nanoparticles are capable of penetrating into the interior of the plaque;
exposing the vulnerable plaque site to either blue-green or red light; and, subsequently, exposing the vulnerable plaque site to light of the other excitation wavelength.

In an aspect of this invention, the first and second plurality of nanoparticles are independently selected from the group consisting of micelles, liposomes, niosomes, polymersomes, polymeric nanoparticles, nanoconjugates and any combination thereof.

In an aspect of this invention, the first plurality of nanoparticles, the second plurality of nanoparticles or the first and the second plurality of nanoparticles comprise a low molecular weight tri-block copolymer having hydrophilic and hydrophobic blocks.

In an aspect of this invention, the tri-block copolymer is PEO-PEE-PMCL.

In an aspect of this invention, the first plurality of nanoparticles, the second plurality of nanoparticles or the first and the second plurality of nanoparticles further comprise one or more non-PDT drugs.

In an aspect of this invention, the non-PDT drug(s) is/are independently selected from the group consisting of an anti-proliferative drug, an anti-inflammatory drug, an anti-thrombotic drug, a pro-healing drug, and a pro-ECM deposition drug.

In an aspect of this invention, the non-PDT drug(s) is/are independently selected from the group consisting of fenofibrate, gluocosteroid, dexamethasone, a statin, Darapladib, LY 518674 and FTY 720.

In an aspect of this invention, at least one non-PDT drug is hydrophilic.

In an aspect of this invention, the hydrophilic drug is selected from the group consisting of bisphosphonate and ApoA1.

In an aspect of this invention, the non-PDT drug(s) is/are a pro-survival protein or an agent selected from the group consisting of IGF-1, bFGF, PDGF, and TGF-β.

In an aspect of this invention, administering the plurality of nanoparticles to the site of the vulnerable plaque comprises local injection at the site of the vulnerable plaque or infusion into the site of the vulnerable plaque from a delivery device.

In an aspect of this invention, the delivery device comprises a balloon, porous balloon or double denuded balloon which is infused or coated with the nanoparticles.

In an aspect of this invention, the first and second plurality of nanoparticles comprise a natural, semi-synthetic or synthetic biocompatible, biodegradable polymer.

In an aspect of this invention, the biocompatible, biodegradable polymer is selected from the group consisting of dextran and copolymers thereof, alginate, cellulose, hyaluronan, chitosan, collagen, elastin, albumin, gelatin, PVP, PEG, PLGA, L-PLGA, PLGA-PEG, PCL, polyanhydrides, PEA, P(LLA-GA-CL), P(LA-GA-CL), P(LLA-CL), and polyacrylic acid.

In an aspect of this invention, the surface of the nanoparticle comprises Annexin V or Protein G.

In an aspect of this invention, the Annexin V is labeled with technetium-99m.

In an aspect of this invention, the surface of the nanoparticles is modified using a substance selected from the group consisting of sialoprotein, ICAM specific ligand and VCAM specific ligands.

DETAILED DESCRIPTION

Definitions

Use of the singular herein includes the plural and vice versa unless expressly stated to be otherwise. That is, "a" and "the" refer to one or more of whatever the word modifies. For example, "a drug" may refer to one drug, two drugs, etc. Likewise, "the polymer" may mean one polymer or a plurality of polymers.

As used herein, unless specified otherwise, any words of approximation such as without limitation, "about," "essentially," "substantially" and the like mean that the element so modified need not be exactly what is described but can vary from the description by as much as ±15% without exceeding the scope of this invention.

As used herein, the use of "preferred," "preferably," or "more preferred," and the like refer to modify an aspect of the invention refers to preferences as they existed at the time of filing of the patent application.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves, foramen ovale closure devices, cerebrospinal fluid shunts, and intrauterine devices. An implantable medical device specifically designed and intended solely for the localized delivery of a therapeutic agent is within the scope of this invention.

As used herein, a "catheter-based" drug delivery device refers to any manner of carrier device that can be delivered to a target region in the vasculature of a patient by means of a catheter such as, without limitation, a self-expandable stent, a balloon-expandable stent, a single diameter balloon, a multi-diameter balloon, a doubly denuded balloon and an injector mechanism located at the distal end of a catheter.

As used herein, "loading" a pharmaceutical formulation on a catheter-based drug delivery device refers to coating a device at the distal end of a catheter with the formulation or with a carrier polymer in which the formulation is dispersed prior to delivery to the intended delivery location. Examples of this form of loading is the well-known drug-eluting stent or DES although other equally well-known devices are know in the art and are encompassed by the present invention. Loading also refers to the location of a delivery device, such as, without limitation, a microporous balloon to an intended target site and then transporting the pharmaceutical formulation from another location in the catheter or even from outside the catheter through a lumen in the catheter to the delivery device.

As used herein, a "vascular disease" refers to a disease of the vessels, primarily arteries and veins, which transport blood to and from the heart, brain and peripheral organs such as, without limitation, the arms, legs, kidneys and liver. In particular "vascular disease" refers to the coronary arterial system, the carotid arterial system and the peripheral arterial system. The disease that may be treated is any that is amenable to treatment with a therapeutic agent, either as the sole treatment protocol or as an adjunct to other procedures such as surgical intervention. The disease may be, without limitation, atherosclerosis, vulnerable plaque, restenosis or peripheral arterial disease.

Various aspects of the present invention encompass formulations for the treatment of atherosclerosis and other vascular diseases.

"Atherosclerosis" refers to the depositing of fatty substances, cholesterol, cellular waste products, calcium and fibrin on the inner lining or intima of an artery. Smooth muscle cell proliferation and lipid accumulation accompany the deposition process. In addition, inflammatory substances that tend to migrate to atherosclerotic regions of an artery are thought to exacerbate the condition. The result of the accumulation of substances on the intima is the formation of fibrous (atheromatous) plaques that occlude the lumen of the artery, a process called stenosis. When the stenosis becomes severe enough, the blood supply to the organ supplied by the particular artery is depleted resulting in strokes, if the afflicted artery is a carotid artery, heart attack if the artery is a coronary artery or loss of organ function if the artery is peripheral.

"Atherosclerotic plaque" or "vulnerable plaque" refers to an atheromatous plaque that has the potential of causing a thrombotic event and is usually characterized by a very thin wall separating it from the lumen of an artery. The thinness of the wall renders the plaque susceptible to rupture. When the plaque ruptures, the inner core of usually lipid-rich plaque is exposed to blood, with the potential of causing a potentially fatal thrombotic event through adhesion and activation of platelets and plasma proteins to components of the exposed plaque.

The phenomenon of vulnerable plaque has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect vulnerable plaque growth into the arterial wall.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, whose reduced concentration combined with macrophage-derived enzyme degradation can cause the fibrous cap of these lesions to rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

"Restenosis" refers to the re-narrowing or blockage of an artery at or near the where angioplasty or another surgical procedure was previously performed to remove a stenosis. It is generally due to smooth muscle cell proliferation at times accompanied by thrombosis.

Peripheral vascular diseases are generally caused by structural changes in blood vessels caused by such conditions as inflammation and tissue damage. A subset of peripheral vascular disease is peripheral artery disease (PAD). PAD is a condition that is similar to carotid and coronary artery disease in that it is caused by the buildup of fatty deposits on the lining or intima of the artery walls. Just as blockage of the carotid artery restricts blood flow to the brain and blockage of the coronary artery restricts blood flow to the heart, blockage of the peripheral arteries can lead to restricted blood flow to the kidneys, stomach, arms, legs and feet.

As used herein, "therapeutic agent," "drug," "active agent," and "bioactive agent," which will be used interchangeably, refer to any substance that, when administered in a therapeutically effective amount to a patient (human or animal) suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

Suitable therapeutic agents include, without limitation, antiproliferative agents, anti-inflammatory agents, antineoplastics and/or antimitotics, antiplatelet, anticoagulant, antifibrin, and antithrombin drugs, cytostatic or antiproliferative agents, antibiotics, antiallergic agents, antioxidants and other bioactive agents known to those skilled in the art.

Suitable antiproliferative agents include, without limitation, actinomycin D, or derivatives or analogs thereof, i.e., actinomycin D is also known as dactinomycin, actinomycin IV, actinomycin $I_1$, actinomycin $X_1$, and actinomycin $C_1$. Antiproliferative agents can be natural proteineous agents such as a cytotoxin or a synthetic molecule, all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives and analogs include 40-O-(2-hydroxyethyl)rapamycin (EVEROLIMUS®), 40-O-(3-hydroxypropyl)rapamycin, 40-O-[2-(2-hydroxy)ethoxy]ethyl-rapamycin, 40-O-tetrazolylrapamycin, or 40-epi-(N1-tetrazolyl)-rapamycin, prodrugs thereof, co-drugs thereof, and combinations thereof.

Suitable anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Suitable antineoplastics and/or antimitotics include, without limitation, paclitaxel, docetaxel, methotrexate, azathioprine, vincristine, vinblastine, fluorouracil, doxorubicin hydrochloride, and mitomycin.

Suitable antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä (Biogen, Inc., Cambridge, Mass.), calcium channel blockers (such as nifedipine), colchicine, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other bioactive substances or agents that may be appropriate include alpha-interferon, and genetically engineered epithelial cells.

Suitable cytostatic or anti-proliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Other suitable bioactive agents include, without limitation, alpha-interferon, genetically engineered epithelial cells, dexamethasone and its derivatives, rapamycin derivatives and analogs such as 40-O-(2-hydroxyethyl)rapamycin (EVEROLIMUS®), 40-O-(3-hydroxypropyl)rapamycin, 40-O-[2-(2-hydroxyethoxy)]ethyl-rapamycin, and 40-O-tetrazolylrapamycin, synthetic inorganic and organic compounds, proteins and peptides, polysaccharides and other sugars, lipids, and DNA and RNA nucleic acid sequences having therapeutic, prophylactic or diagnostic activities, nucleic acid sequences include genes, antisense molecules which bind to complementary DNA to inhibit transcription, and ribozymes. Some other examples of suitable bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

As used herein, "pro-healing" refers to a moiety that aids in the healing process at the site of implantation of a medical device of this invention. Useful pro-healing moieties include, without limitation, endothelial progenitor cells, nitric oxide, vascular endothelial growth and 17-β-estradiol.

As used herein, "treating" refers to the administration of a therapeutically effective amount of a therapeutic agent to a patient (human or animal) known or suspected to be suffering from a disease. A "therapeutically effective amount" refers to that amount of a therapeutic agent that will have a beneficial affect, which may be curative or palliative, on the health and well-being of the patient with regard to the disease with which the patient is known or suspected to be afflicted.

As used herein, a polymer is a molecule made up of the repetition of a simpler unit, herein referred to as a constitutional unit. The constitutional units themselves can be the product of the reactions of other compounds. A polymer may comprise one or more types of constitutional units. As used herein, the term polymer refers to a molecule comprising 2 or more constitutional units. Polymers may be straight or branched chain, star-like or dendritic, or one polymer may be attached (grafted) onto another. Polymers may be cross-linked to form a network.

As used herein, "copolymer" refers to a polymer which includes more than one type of constitutional unit.

As used herein, "biocompatible" refers to a material that in its original intact state and when biologically decomposed into its degradation products is not toxic or at least is minimally toxic to living tissue. A biocompatible material does not, or at least minimally and reparably, injure living tissue. Further, a biocompatible material does not or at least minimally and controllably cause an immunological reaction in living tissue.

As used herein, the terms "biodegradable," "bioerodable," "bioabsorbable," and "degraded," which are used interchangeably, refer to polymers, particles, and materials, that are capable of being completely, or substantially completely, degraded, dissolved, and/or eroded over time when exposed to physiological conditions (pH, temperature, and fluid or other environment), and can be gradually resorbed, absorbed and/or eliminated by the body, or that can be degraded into fragments that can be eliminated from the body by the kidneys.

As used herein, "degradation time," "biodegradation time," and "absorption time," are used interchangeably, and refer to the time for a biodegradable material implanted in a host animal to substantially, preferably completely, biodegrade in vivo.

As used herein, 'biostable" refers to a material that does not appreciably decompose in a physiological environment, for example, without limitation, at physiological pHs or in the presence of enzymes.

As used herein, a "synthetic polymer" refers to one that is created wholly in the laboratory while a semi-synthetic polymer refers to a naturally-occurring polymer than has been chemically modified in the laboratory.

As used herein, "hydrophobic" refers to a substance that lacks an affinity for water. That is, it tends to repel water, to not dissolve in, mix with or be wetted by water or to do so only to a very limited degree and to not absorb water or, again, to do so only to a very limited degree. With regard to polymers, generally hydrophobicity increase with increasing alkyl content in the polymer backbone, that is, the greater the alkyl content in one or more of the constitutional units of the polymer. The hydrophobicity of a polymer may be characterized by determining the static contact angle of droplets of distilled water on a surface of the polymer. The greater the contact angle, the more hydrophobic the polymer. Generally speaking, a contact angle of greater than 90° indicates a hydrophobic polymer. The specifics or such measurements will not be presented here since they are well-known to those skilled in the art.

To the contrary, "hydrophilicity" refers to a substance that has an affinity for water and tends to attract, dissolve in, be miscible with or be wetted by water.

As used herein, "contact angle" is defined as an angle at the tangent of a droplet in a fluid phase that has taken an equilibrium shape on a solid surface under ambient condition.

Hydrophobicity can be gauged using the Hildebrand solubility parameter δ. The value of δ relates to the cohesive energy density of a substance and is calculated using the equation:

$$\delta = (\Delta E/V)^{1/2}$$

where δ is the solubility parameter in units of $(cal/cm^3)^{1/2}$; ΔE is the energy of vaporization, cal/mole; and V is the molar volume in units of $cm^3$/mole.

Whether a particular material is hydrophobic or hydrophilic relative to another material is relative. That is, as between different materials, whichever has the lower δ value compared to that of the other is designated as being hydrophobic and the material with higher δ value is designated as being hydrophilic. For the purposes of this invention, however, in one embodiment the δ value defining a boundary between hydrophobic and hydrophilic is arbitrarily set at between about 9.9 and 10.1 $(cal/cm^3)^{1/2}$. According to this embodiment, hydrophobic is defined as having a δ value equal to or below about 9.9 $(cal/cm^3)^{1/2}$, and hydrophilic is defined as having a δ value of about 10.1 $(cal/cm^3)^{1/2}$ or higher. Materials having a δ value between about 9.9 and about 10.1 $(cal/cm^3)^{1/2}$ can exhibit behavior characterized as being both hydrophilic and hydrophobic. Such materials are termed "amphiphilic."

Suitable hydrophobic polymers include, without limitation, poly(vinyl acetate), poly(ethylene-co-vinyl acetate), poly(vinyl acetals) such as poly(vinyl butyral) (e.g., BUTVAR), poly(meth)acrylates, for example, poly(methyl methacrylate), poly(ethyl methacrylate), poly(n-propyl methacrylate), poly(iso-propyl methacrylate), poly(n-butyl methacrylate), copolymers of butyl n-methacrylate with non-polar monomers (e.g., poly(ethyl methacrylate-co-n-butyl methacrylate)), poly(iso-butyl methacrylate), poly(methyl acrylate), poly(ethyl acrylate), poly(n-propyl acrylate), poly(iso-propyl acrylate), poly(n-butyl acrylate), poly(iso-butyl acrylate), styrene-butadiene-styrene triblock copolymers, styrene-ethylene/butylene-styrene triblock copolymers (e.g., KRATON available from Shell Oil Co. of Houston, Tex.), styrene-isobutylene-styrene triblock copolymers, parylene-C, organosilicon polymers (e.g., ELASTEON), and halogenated (e.g., fluorinated or chlorinated) polymers such as poly(vinyl chloride), poly(vinyl fluoride), poly(vinylidene chloride), poly(vinylidene fluoride) (e.g., KYNAR available from Atofina Chemicals, Inc. of Philadelphia, Pa.), poly(hexafluoropropene), poly(vinylidene fluoride-co-hexafluoropropene) (e.g., SOLEF available from Solvay S.A. of Brussels, Belgium), poly(ethylene-co-hexafluoropropene), and various grades of amorphous TEFLON, including polytetrafluoroethylene (available from E.I. Du Pont de Nemours & Co. of Wilmington, Del.), BUTVAR is a trade name of poly(vinyl butyral) (available from Solutia, Inc. of St. Louis, Mo.), ELASTEON is the trade name of the block copolymer of methylene diphenyl diisocyanate, 1,4-butanediol, polyhexamethyleneglycol, and a carbinol terminated polydimethylsiloxane (manufactured by AorTech Biomaterials Co. of Chatswood, Australia), poly[trimellitylimido-L-tyrosine-co-sebacic acid-co-1,3-bis(para-carboxyphenoxy)propane] p(TMIT-SBA-PCPP), poly[1,6-bis(para-carboxyphenoxy)-hexane-co-di-ortho-carboxyphenoxy sebacateanhydride] p(PCPX-OCPSA), poly[1,3-bis(para-carboxyphenoxy) propane-co-salicylic acid-co-sebacic acid] p(PCPP-SBA-SA), poly(maleic acid-co-sebacic acid), p(MA-SBA), poly(L-lactic acid-co-L-aspartic acid), p(LLA-LAspA), poly(DL-lactic acid-co-L-aspartic acid) p(DLLA-LAspA), poly(L-lactic acid) pLLA, poly(DL-lactic acid) pDLLA, poly(L-lactic acid-co-ethylene glycol) p(LLA-EG), poly(DL-lactic acid-co-ethylene glycol) p(DLLA-EG), poly(ethylene glycol-co-butylene terephthalate) p(EG-BT), poly(4-hydroxy-L-proline ester) p(HOXPE), poly(1,10-decanediol-co-L-lactic acid) p(DCD-LLA), poly(1,10-decanodiol-co-D,L-lactic acid) p(DCD-DLLA), poly(1,2,6-hexanetriol-co-trimethylorthoacetate) p(HTOL-TMAC), poly(hydroxybutyrate) (PHB), poly(hydroxyvalerate) (PHV), poly(hydroxy-butyrate-valerate) (PHBV), poly(L-lactide-co-ε-caprolactone) and poly(L-lactide-co-trimethylene carbonate).

As used herein, "hemocompatible" refers to the propensity of a material to cause no harm to blood or blood components. In general, the tests set forth in ISO (international Organization for Standardization) 10993 may be employed to ascertain the level of hemocompatibility of a particular material.

A "pharmaceutically acceptable composition" refers to composition that does not cause significant irritation to an organism to which it is administered and does not abrogate the biological activity and properties of the therapeutic agent. The term "composition" and the term "formulation" may be used interchangeably.

As used herein, "particle" refers to a micro- or macroscopic bit of material ranging in size from one-tenth of a nanometer to several centimeters in size as measured through-particle along the longest axis or as measured by particle diameter for spherical or nearly spherical particles. A particle may include one or more types of constituent molecules. As used herein, particles include core-shell structures such as micelles, worm micelles, niosomes, liposomes, and polymersomes and solid structures such as q-dots, nanocrystals, and solid or porous bits of material of the indicated dimensions.

With regard to spherical or near spherical particles, a well-known means for determining the average diameter of a plurality of particles is by dynamic light scattering (DLS), also referred to as photon correlation spectroscopy, which measures the diffusion of the particles in solution. Several other means of determining particle diameter are known in the art as is the relationship of an average particle size as determined by one of these means compared to the others. For the purposes of this invention, any reference to average particle diameter refers to that average as determined by DLS and those skilled in the art will know how to relate such diameters to those resulting from other measurement protocols.

For non-spherical particles, reference to a "diameter" in fact refers to the diameter of an equivalent spherical particle, that is, a spherical particle which would provide the same results if subjected to the same measurement technique. For example, photon correlation spectroscopy measures hydrodynamic diameter, and therefore, the diameter reported is that of a spherical particle with the same hydrodynamic diameter as that of the irregularly shaped particle.

As used herein, a "nanoparticle" refers to a particle with a maximum cross-sectional, i.e., through-particle rather than along the surface, dimension or diameter if the nanoparticle is essentially spherical of from 1 nm to 1000 nm.

A "microparticle" refers to a particle with a maximum cross-sectional dimension or diameter if appropriate of from 1 um to about 1000 um.

As used herein, a material that is described as a layer, film or coating (for the purposes of this invention, the terms are used interchangeably) "disposed over" a substrate refers to such coating deposited directly or indirectly over at least a portion of the surface of the substrate. Direct depositing means that the coating is applied directly to the surface of the substrate. Indirect depositing means that the coating is applied to an intervening layer that has been deposited directly or indirectly over the substrate.

A "micelle" is a spherical colloidal nanoparticle spontaneous formed by many amphiphilic molecules in an aqueous medium when the Critical Micelle Concentration (CMC) is exceeded. Amphiphilic molecules have two distinct components, differing in their affinity for a solute, most particularly water. The part of the molecule that has an affinity for water, a polar solute, is said to be hydrophilic. The part of the molecule that has an affinity for non-polar solutes such as hydrocarbons is said to be hydrophobic. When amphiphilic molecules are placed in water, the hydrophilic moiety seeks to interact with the water while the hydrophobic moiety seeks to avoid the water. To accomplish this, the hydrophilic moiety remains in the water while the hydrophobic moiety is held above the surface of the water in the air or in a non-polar, non-miscible liquid floating on the water. The presence of this layer of molecules at the water's surface disrupts the cohesive energy at the surface and lowers surface tension. Amphiphilic molecules that have this effect are known as "surfactants." Only so many surfactant molecules can align as just described at the water/air or water/hydrocarbon interface. When the interface becomes so crowded with surfactant molecules that no more can fit in, i.e., when the CMC is reached, any remaining surfactant molecules will form into spheres with the hydrophilic ends of the molecules facing out, that is, in contact with the water forming the micelle corona and with the hydrophobic "tails" facing toward the center of the of the sphere. Drugs suspended in the aqueous medium can be entrapped and solubilized in the hydrophobic center of micelles.

Micelles formed from relatively low molecular weight surfactants generally have a CMC that is usually quite high so that the formed micelles dissociate rather rapidly upon dilution, i.e., the molecules head for open places at the surface of the water with the resulting precipitation of the drug. This short-coming can be avoided by using lipids with a long fatty acid chain or two fatty acid chains, specifically phospholipids and sphingolipids, or polymers, specifically block copolymers to form the micelles.

Polymeric micelles have been prepared that exhibit CMCs as low as $10^{-6}$ M (molar). Thus, they tend to be very stable while at the same time showing the same beneficial characteristics as surfactant micelles. Any micelle-forming polymer presently known in the art or as such may become known in the future may be used in the method of this invention. Examples of micelle-forming polymers are, without limitation, methoxy poly(ethylene glycol)-b-poly(ε-caprolactone), conjugates of poly(ethylene glycol) with phosphatidylethanolamine, poly(ethylene glycol)-b-polyesters, poly(ethylene glycol)-b-poly(L-aminoacids), poly(N-vinylpyrrolidone)-bl-poly(orthoesters), poly(N-vinylpyrrolidone)-b-polyanhydrides and poly(N-vinylpyrrolidone)-b-poly(alkyl acrylates).

In addition to the classical spherical micelles described above, there are "worm micelles." Worm micelles, as the name suggests, are cylindrical in shape rather than spherical. They are prepared by varying the weight fraction of the hydrophilic polymer block to the total block copolymer molecular weight in the hydrophilic polymer-b-hydrophobic polymer structure discussed above for preparing spherical micelles. Worm micelles have the potential advantage of not only being bio-inert and stable as are spherical polymeric micelles but also of being flexible. Polyethylene oxide has been used extensively to create worm micelles with a number of hydrophobic polymers such as, without limitation, poly(lactic acid), poly(ε-caprolactone), poly(ethyl ethylene) and polybutadiene. A representative description of worm micelle formation, characterization and drug loading can be found in Kim, Y., et al., *Nanotechnology,* 2005, 16:S484-S491.

A "liposome" is a core/shell construct in which the shell comprises a bilayer rather than a monolayer. Liposomes may be unilamellar, composed of a single bilayer, or they may be multilamellar, composed of two or more concentric bilayers. A phospholipid bilayer is formed from two layers of phospholipid molecules.

Phospholipids are molecules that have two primary regions, a hydrophilic head region comprised of a phosphate of an organic molecule and one or more hydrophobic fatty acid tails. In particular, naturally-occurring phospholipids have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, known as a phospholipid bilayer or a lamella, converge into a sphere and in doing so entrap some of the aqueous medium, and whatever may be dissolved or suspended in it, in the core of the sphere. Examples of phospholipids that may be used to create liposomes are, without limitation, 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)] sodium salt, 1,2-dimyristoyl-sn-glycero-3-[phospho-L-serine] sodium salt, 1,2-dioleoyl-sn-glycero-3-phosphoethanolamine-N-glutaryl sodium salt and 1,1',2,2'-tetramyristoyl cardiolipin ammonium salt.

Liposomes may be unilamellar, composed of a single bilayer, or they may be multilamellar, composed of two or more concentric bilayers. Liposomes range from about 20 nm-100 nm diameter for small unilamellar vesicles (SUVs), about 100 nm-5000 nm for large multilamellar vesicles and ultimately to about 100 microns for giant multilamellar vesicles (GMVs). LMVs form spontaneously upon hydration with agitation of dry lipid films/cakes which are generally formed by dissolving a lipid in an organic solvent, coating a vessel wall with the solution and evaporating the solvent. Energy is then applied to convert the LMVs to SUVs, LUVs, etc. The energy can be in the form of, without limitation, sonication, high pressure, elevated temperatures and extrusion to provide smaller single and multi-lamellar vesicles. During this process some of the aqueous medium is entrapped in the vesicle. Generally, however, the fraction of total solute and therefore the amount of drug entrapped tends to be rather low, typically in the range of a few percent. Recently, however, liposome preparation by emulsion templating (Pautot, et al., *Langmuir,* 2003, 19:2870) has been shown to result in the entrapment of virtually 100% of aqueous solute. Emulsion templating comprises, in brief, the preparation of a water-in-oil emulsion stabilized by a lipid, layering of the emulsion onto an aqueous phase, centrifugation of the water/oil droplets into the water phase and removal of the oil phase to give a dispersion of unilamellar liposomes. This method can be used to make asymmetric liposomes in which the inner and outer monolayers of the single bilayer contain different lipids. Liposomes comprising phospho- and/or sphingolipids may be used to deliver hydrophilic (water-soluble) or precipitated therapeutic compounds encapsulated within the inner liposomal volume and/or to deliver hydrophobic drugs dispersed within the hydrophobic core of the bilayer membrane.

A core/shell construct similar to that of a liposome but made of polymers other than phospholipids or sphigolipids is called a "polymersome." Block copolymers may be used to form polymersomes. Depending on the length and chemical nature of the polymers in the diblock copolymer, polymersomes can be substantially more robust that liposomes. In addition, the ability to control completely the chemical nature of each block of the diblock copolymer permits tuning of the polymersome's composition to fit the desired application. For example, membrane thickness can be controlled by varying the degree of polymerization of the individual blocks. Adjusting the glass transition temperatures of the blocks will affect the fluidity and therefore the permeability of the membrane. Even the mechanism of release can be modified by altering the nature of the polymers.

Polymersomes can be prepared in the same manner as liposomes. That is, a film of the diblock copolymer can be formed by dissolving the copolymer in an organic solvent, applying a film of the copolymer-containing solvent to a vessel surface, removing the solvent to leave a film of the copolymer and then hydrating the film. This procedure, however, tends to result is a polydispersion of micelles, worm micelles and vesicles of varying sizes. Polymersomes can also be prepared by dissolving the diblock copolymer in a solvent and then adding a poor solvent for one of the blocks, which will result in the spontaneous formation of polymersomes.

As with liposomes, polymersomes can be used to encapsulate therapeutic agents by including the therapeutic agent in the water used to rehydrate the copolymer film. Polymersomes can also be force-loaded by osmotically driving the therapeutic agent into the core of the vesicle. Also as with liposomes, the loading efficiency is generally low. Recently, however, a technique has been reported that provides polymersomes of relative monodispersity and high loading efficiency; generation of polymerisomes from double emulsions. Lorenceau, et al., *Langmuir,* 2005, 21:9183-86. The technique involves the use of microfluidic technology to generate double emulsions consisting of water droplets surrounded by a layer of organic solvent. These droplet-in-a-drop structures are then dispersed in a continuous water phase. The diblock copolymer is dissolved in the organic solvent and self-assembles into proto-polymersomes on the concentric interfaces of the double emulsion. The actual polymersomes are formed by completely evaporating the organic solvent from the shell. By this procedure the size of the polymersomes can be finely controlled and, in addition, the ability to maintain complete separation of the internal fluids from the external fluid throughout the process allows extremely efficient encapsulation.

Particles may be nano-particles or micro-particles. Particles may have active agents mixed, dispersed, or dissolved or otherwise incorporated in the particle material. Microparticles and nanoparticles can be made of any biocompatible material including, but not limited to a natural, semi-synthetic or synthetic polymers, metals, ceramics or glasses. The particle material can be biostable and/or biodegradable, but biodegradable particles are presently preferred. If biodegradable materials are used in the production of particles, the particles may degrade in days, weeks, or months.

Polymeric particles with drug distributed throughout may be referred to as matrix type or monolithic type drug delivery particles. The drug may be homogeneous, or substantially homogeneous, throughout the matrix particle, or the drug distribution may be non-uniform. The drug may be released by any number of mechanisms. In some embodiments, the material dissolves, and the drug may be released as it does so. In other embodiments, the drug may diffuse through the matrix material, and/or diffuse through pores formed when the drug is dissolved from the matrix closer to the surface.

The particles can also encapsulate one or more active agents by having an outer shell of polymer, metal, or ceramic or a combination thereof, with an inner compartment containing the agent(s). If the outer shell does not contain a drug, it may serve as a rate-controlling membrane as the drug must diffuse through the membrane to reach its target In still other aspects, the exterior coating or layer may dissolve or biodegrade over time resulting in release of the drug.

There are various well-known methods by which the solid matrix particles or reservoir type particles of this invention can be fabricated including, without limitation, emulsion solvent evaporation methods, phase separation methods, interfacial methods, extrusion methods, molding methods, injection molding methods, heat press methods, coating or layering processes, spray drying, electrospraying, membrane emulsion and precision particle fabrication.

The formulations of the present invention may be delivered by any number of mechanisms including intravenous injection or infusion, minimally invasive coronary injection, use of a drug delivery catheter, use of a coated balloon or a coated stent.

Delivery may be systemic or local. Systemic delivery involves the administration of a therapeutic agent at a discrete location usually remote from the target site followed by the dispersal of the agent throughout the patient's body including, of course, to the target treatment site or organ. In the context of the present invention, systemic delivery may be carried out by introduction of the therapeutic agent into the vascular system (parenteral administration) directly such as injection into a vein or an artery. The injection may be a bolus injection (all delivered over a short period of time) or an infusion over a specified time period. Systemic delivery is strongly influenced by the so-called ADMET factors: absorption, distribution, metabolism, excretion and toxicity. Typically, for systemic delivery In order to achieve a therapeutically effective amount of the agent at the afflicted site, it is usually necessary to administer an initial dose substantially greater than the therapeutically effective amount to account for the dilution the agent undergoes as it travels through the body.

Local delivery comprises administration of the therapeutic agent directly to the target site. The initial dose can be at or very close to the therapeutically effective amount. With time, some of the locally delivered therapeutic agent may diffuse over a wider region but such is not the intent of localized delivery and the concentration of the diffused agent will ordinarily be sub-therapeutic, i.e., too low to have a therapeutic effect. Since localized delivery targets only the desired treatment site, it is possible that some of the causal factors of the disease that have spread to as yet non-afflicted regions of the organ at the periphery of the afflicted region may not undergo sufficient treatment, resulting in reoccurrence of the disease. As used herein, the term "local delivery" and the term "regional delivery" may be used interchangeably.

In the context of the present invention, local delivery encompasses local injection to the site, catheter delivery utilizing a catheter with a delivery lumen, minimally invasive coronary injection, use of a drug delivery catheter, use of a coated balloon or a coated stent.

One means for local delivery of the plurality of particles of the present invention is a vascular catheter. A vascular catheter is a thin, flexible tube with a manipulating means at one end, referred to as the proximal end, which remains outside the patient's body, and an operative device at or near the other end, called the distal end, which is inserted into the patient's artery or vein. The catheter is often introduced into a patient's vasculature at a point remote from the target site, e.g., into the femoral artery of the leg where the target is in the vicinity of the heart. The catheter is steered, assisted by a guide wire than extends through a lumen in the flexible tube, to the target site whereupon the guide wire is withdrawn at which time the lumen may be used for the introduction of fluids, often containing therapeutic agents, to the target site.

A vascular catheter may also have a balloon at the end. A "balloon" refers to the well-known in the art device, usually associated with a vascular catheter, that comprises a relatively thin, elastomeric material that when positioned at a particular location in a patient's vessel can be expanded or inflated to an outside diameter that is essentially the same as the inside or luminal diameter of the vessel in which it is placed. Inflation of the balloon may be effected by any means known or as shall become known in the art. At present, a balloon of this invention may be inflated using a liquid medium such as water or isotonic saline solution.

A balloon of this invention may have substantially a single diameter over its entire length such that the full length of the balloon is in contact with the luminal surface of the vessel.

A balloon of this invention may also comprise two different outside diameters. At each end of the balloon is a first diameter, which is the same as the diameter of the single diameter balloon described above. Between the end first diameters may be any number of additional first diameters. Each such first diameter is separated from each other such diameter by a second diameter which is less than the inside diameter of the vessel and therefore does not contact the luminal surface. Use of the term "a second diameter" is nominal; the point is that there are regions between the first diameters that are not in contact with the luminal surface and the diameters of those regions may be identical or all may be different; for the purposes of this discussion it is assumed that they are all the same.

A balloon of this invention may comprise a coating on all or part of its surface, the coating being the delivery interface of this invention. Coated balloons are well-known in the art for the localized delivery of therapeutic agents and any coating construct known or as may in the future become known may be used in the method of this invention.

Rather than or in addition to being coated, a balloon of this invention may be microporous. A microporous balloon comprises a thin membrane in which a large number; e.g., hundreds, thousands even millions of holes of substantially uniform size have been created. The holes can range in size from tens of nanometers to microns and can be created by a number of techniques including, but not limited to, laser drilling and ab initio synthesis. In the latter case, the membrane is synthesized from molecules that assemble in such a manner than voids are left in the structure formed. A microporous balloon formed by these or any other procedure may be used in the method of this invention.

When using a microporous balloon, the therapeutic agent or agents are delivered to the balloon at the distal end of a catheter in the fluid used to expand the balloon. When the balloon is expanded, rather than simply leaking out of the balloon in an uncontrolled manner, the size of the holes results in a slow, controlled "weeping" of fluid from the holes and carried along with the fluid are the therapeutic agents. The fluid and therapeutic agents then spread out over the surface of the balloon in a thin film and when the surface of the balloon is contacted with the luminal surface of a vessel, the therapeutic agents are brought into contact with the luminal surface and held there until they penetrate the surface of the vessel wall.

If a balloon having two or more diameters as discussed above is used, the microporous regions may be only the portions that are in contact with the luminal surface (those represented by the first diameter), only those portions not in contact with the luminal surface (those in the area of the second diameter), or both regions may be microporous, or only those regions with the regions characterized by the second diameter are non-porous.

Aspects of the present invention encompass methods of treatment with a therapeutically effective amount of an active agent wherein the active agent comprises a plurality of particles as described above. The plurality of particles may be included in one formulation blended in two or more formulations. The methods of administration or delivery include not only those mentioned above but any other method known now or as may become available in the future.

Encompassed within the various aspects of the present invention are methods of treatment in which some particles are administered regionally or locally. The patient treated may be any animal, but preferably a mammal, and more preferably, a human.

Various types of materials may be used to manufacture the particles of the present invention. Examples include, but are not limited to natural, semi-synthetic or synthetic polymers, metals, ceramics or glasses.

Among useful biocompatible, relatively biostable polymers are, without limitation, polyacrylates, polymethacrylates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers include naturally-occurring polymers such as, without limitation, collagen, chitosan, alginate, fibrin, fibrinogen, alginates, cellulosics, starches, dextran, dextrin, hyaluronic acid, heparin, glycosaminoglycans, polysaccharides and elastin.

Synthetic biocompatible, biodegradable polymers include, without limitation, polylactic acid, polyglycolic acid, polyethylene glycol, polycaprolactone, polyanhydrides, polyvinyl alcohol and poly(ester-amides).

Examples of synthetic polymers include, without limitation, polyphosphazines, polyphosphoesters, polyphosphoester urethane, polyhydroxyacids, polyhydroxyalkanoates, polyanhydrides, polyesters, polyorthoesters, polyamino acids, polyoxymethylenes, poly(ester-amides) and polyimides.

Other polymers which may be suitable for use include, without limitation, poly(L-lactide), poly(D-lactide), poly(D,L-lactide), poly(meso-lactide), polyglycolide, poly(L-lactide-co-D,L-lactide), poly(L-lactide-co-glycolide), poly(D-lactide-co-glycolide), poly(D,L-lactide-co-glycolide), poly(meso-lactide-co-glycolide), poly(hydroxyvalerate), poly(hydroxybutyrate), poly(ethylene glycol-co-butylene terephthalate) (POLYACTIVE®), poly(hydroxybutyrate), poly(hydroxybutyrate-co-valerate), polydioxanone, polyorthoester, poly(glycolic acid-cotrimethylene carbonate), cyanoacrylates, poly(trimethylene carbonate), poly(iminocarbonate), copoly(ether-esters), polyalkylene oxalates, polyphosphazenes, polyiminocarbonates, polycarbonates, parylene, polyethylene, polyethylene teraphthalate, ethylene vinyl acetate, silicone, polyethylene oxide, poly(ethylene-co-vinyl alcohol), polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; polyvinylpyrrolidone (PVP), rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Embodiments

In the following discussing the acronyms below may appear:
ICAM refers to Inter Cellular Adhesion Molecule.
VCAM refers to Vascular Cell Adhesion Molecule.
DSPG refers to distearoyl-L-α-phosphatidylglycerol.
DSPE refers to distearoylphosphatidylethanolamine.
DSPC refers to distearoylphosphatidylcholine.
DMSO refers to Dimethyl Sulfoxide.
NMP refers to N-Methylpyrrolidone.
PEE refers to polyethylethylene.
PMCL refers to poly(γ-methyl-ε-caprolactone).

The formulation and method provided herein can be used specifically for PDT drugs delivery to all sorts of tissue including malignant, non-malignant tissue, ischemic myocardium, high lipid plaque, or inflamed cells.

In one embodiment is provided a PDT drug formulation comprising a nanoparticle such as a liposome, a polymersome, or a micelle wherein the PDT drug is adhered to or encapsulated within the nanoparticle. Also provided is a method of delivering of the PDT drug formulation via a porous balloon or a double denuded balloon to the lumen side of vascular tissues.

In one embodiment, the PDT drug loaded liposome or polymersome has a diameter of about 40 nm to about 800 nm. Due to leakiness and fatty characteristic of the diseased tissues compare to healthy tissue, the liposome or polymersome especially those of about 175 nm to about 300 nm in size will partition preferentially into diseased vessel tissue by size exclusion. Upon decomposition of the PDT carrier, the hydrophobic PDT drug further partitions itself into fatty tissues. In some embodiments, the liposome will be designed with low stability, including absence of cholesterol, to allow for fast solubilization of drug which is then quickly taken into tissue.

In one embodiment, PDT drug-loaded liposomes or polymersomes with negatively charged surfaces are made of, without limitation, DSPG, DSPE, DSPC or long chain fatty acid such as oleic acid. The PDT drug loaded liposome or polymersome has preferentially higher uptake in diseased tissue because healthy endothelium cells have more inherent negative charge and therefore repels materials with negative charges.

Figure 1:
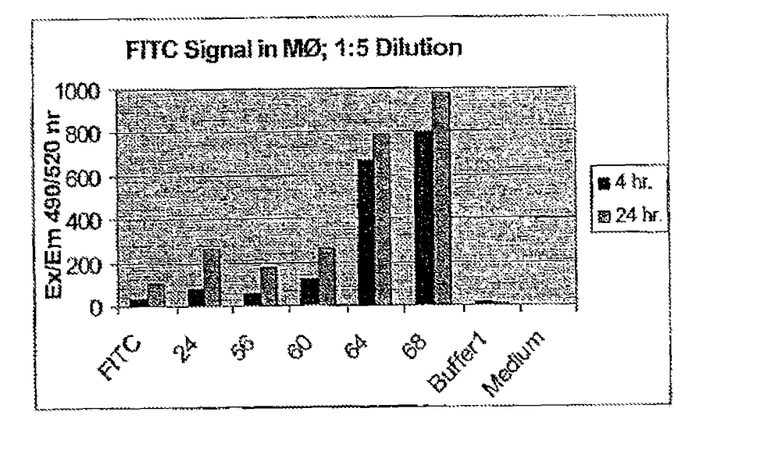
FIG. 1 shows that increasing the negative charge on liposomes increases their uptake by macrophages.

In one embodiment, the PDT drug-loaded negatively charged liposomes or polymersomes also includes on their surfaces ceramide. This combination has higher uptake by macrophages. Referring to the experiment below and FIG. 1, increasing the negative charge on liposome (formulations F-24, F-56, F-60 and F-64 bear increasing negative charge as indicated by Zeta potential) increases uptake of liposomes by macrophages.

TABLE 1

| Formulation Code | Formulation | Formulation Molar Ratio | Zeta Potential (meV) |
| --- | --- | --- | --- |
| F - 24 | DSPG:DSPC:Chol:Ceramide | 1:3:1:3% | −27.163 |
| F - 56 | DSPG:DSPC:Chol:Ceramide | 1:2:1:3% | −23.848 |
| F - 60 | DSPG:DSPC:Chol:Ceramide | 1:1.4:1:3% | −30.514 |
| F - 64 | DSPG:DSPC:Chol:Ceramide | 1:1:1:3% | −38.794 |
| F - 68 | DSPG:DSPC:Chol:Ceramide | 1:1:1:3% | −36.668 |

TABLE 2

| Formulation Code | Size (nm) | Polydispersity |
| --- | --- | --- |
| F - 24 | 187 | 0.05 |
| F - 56 | 203 | 0.05 |
| F - 60 | 177 | 0.06 |
| F - 64 | 178 | 0.06 |
| F - 68 | 100 | 0.07 |

In one embodiment is provided a micelle formulation of a PDT drug comprising PEG-PE where the micelle has a diameter of about 10 nm to about 100 nm, preferably about 20 nm to about 40 nm. The formulation has very high penetration into the arterial tissue. The high penetration of micelles into tissues with combination of local delivery will deliver the PDT drug component in high efficiency into the diseased area. In some embodiments the micelle contains anionic carboxylate groups in either the hydrophilic or hydrophobic region of the macromolecule to allow for increased uptake by macrophages.

In one embodiment, the particle is white blood cell or a monocyte obtained from the patient undergoing treatment. The monocyte is labeled with a PDT drug by chemical conjugation to the surface of the monocyte. The loaded monocyte can be introduced through a delivery device to the inflamed area where the monocyte will partition in the diseased area, carrying the PDT drug with it.

In one embodiment, a particulate PDT drug formulation hereof is complexed or covalently conjugated with serum albumin (bovine or human) for increased targeting to lipid rich plaque, macrophages or scavenger receptor.

In one embodiment, a particulate PDT drug formulation hereof is complexed or covalently conjugated with low density lipoprotein (LDL) for increased targeting to the scavenger receptor. An advantage of using LDL is the potential of increasing apoptosis due to intracellular uptake of LDL to sites such as the mitochondria.

In one embodiment, a particulate PDT drug formulation hereof is conjugated with hemoglobin. Advantages of using hemoglobin include the single free cysteine that tends to avoid crosslinking as well as ability to concurrently deliver both a PDT drug and oxygen to the diseased site.

All of the above formulations can be used to deliver any photosensitizer including, without limitation, any texaphyrin, porphyrin, benzochlorin, porphyrazin, porphyrazin derivatives and chlorophil. Alternatively, they can be used to deliver porphyrin precursors such as 5-aminoleuvinic.acid (ALA) and methyl aminolevulinate (MAL).

The above described embodiments are all compatible with wavelength of light ranging from UV to infrared including the range of about 350 nm to about 800 nm, and can be used for delivery of the aforementioned photosensitizers to all sorts of tissue including malignant, non-malignant tissue, and inflamed cells.

In one embodiment is provided a method to prepare PDT drug formulation using polymeric nanoparticles with enhanced uptake and retention in arterial tissues.

In one embodiment, the polymeric nanoparticles having diameters in the range of about 50 nm to about 800 nm can be made of any biodegradable polymers, either natural, semi-synthetic or synthetic in nature.

In another embodiment, the polymeric nanoparticles having diameters of about 100 nm to about 300 nm are used for better tissue penetration. Examples include natural polymer such as dextran and its copolymers, alginate, cellulose, hyaluronan, chitosan, collagen, elastin, albumin, gelatin, PEG, PVP, and synthetic polymers such as PLGA, L-PLGA, PLGA-PEG, PCL, polyanhydrides, PEA, P(LLA-GA-CL), P(LA-GA-CL), P(LLA-CL), poly acrylic acid etc.

In one embodiment, the polymeric nanoparticles can be enhanced with cell and tissue adhesion features as surface modifications. Materials such as, without limitation, fibronectin, collagen, vitronectin, laminin, matrigel, chitosan (to non-chitosan particles), polyacrylates (to non-polyacrylate particles), RGD-peptides, sialo groups etc. can be physically adsorbed onto the particles' surface or can be covalently attached onto the surface. One example of a surface modification that can be used to prepare the surface for covalent attachment of the above materials is radio frequency glow discharge in the presence of ammonia gas, which introduces amine groups onto the surface.

In another embodiment, the above polymeric nanoparticle formulations are mixed with a carrier gel that will function as a glue to stick the particles onto the artery wall thereby greatly improving particle retention. Examples of the carrier gel material are, without limitation, sodium hyaluronate, hyaluronic acid, sodium alginate, carboxymethyl cellulose and other cellulosics, low molecular weight biodegradable polymers, polysaccharides such as dextran, polyvinylpyrrolidone (PVP) and PEG, all of which are hemocompatible.

In one embodiment, the PDT drug polymeric nanoparticle formulations described above are also mixed with penetration enhancers such as DMSO, Cremophor, NMP, EtOH, Hyaluronidase (ISTA Pharmaceutical Halozyme Inc.) or a hyperosmostic containing suspension of drug containing vehicles. The suspension may be rendered hyperosomotic by the addition of a wide range of biocompatible substances such as, without limitation, glucose, mannose, fructose, sucrose, trehalose, monosaccharides, disaccharides, sodium chloride, phosphate salts, salts, glycine, saponin and semi-synthetic derivatives such as DS-1 and Qh-957, EDTA, taurocholic acid, benzalkonium chloride, capric acid, melittin or amino acids.

In one embodiment, the PDT polymeric nanoparticle formulations above can be coated together with the aforementioned gels or with more durable hydrophobic or hydrophilic polymers on an angioplasty balloon. Polymer coating materials can include thin layers of either the aforementioned synthetic materials or with PVDF, plasticized PVP and polyacrylic acid to prevent particle wash-off before balloon expansion.

In addition to vulnerable plaque and acute myocardical infarction (MI), the PDT drug loaded nanoparticles can also be utilized for treatment of in-stent restenosis, as an adjunct for drug eluting stent (DES) applications and the like.

Size and rigidity of liposomal PDT drug affects the permeation of the drug into arterial tissues. Thus, a mixed population of liposomal constructs with various distributions of sizes and rigidity will significantly influence drug uptake into diseased vascular tissue compared to healthy vasculature. Large but more rigid liposomes will be able to penetrate more into diseased vessels than healthy vessels because it is difficult for rigid liposomes to permeate through the intact endothelium of healthy vessels. Small and less rigid liposomes will easily penetrate both healthy and disease vessels wall. Due to the lack of foam cells and macrophages in healthy vessels, liposomes will clear faster from the healthy vessel walls. Thus, a differentiation of liposomal sizes and rigidity will greatly enhance uptake of drug-loaded liposomes into the diseased region compared to healthy vessels.

In one embodiment, micelles of diameter of about 10 nm to about 20 nm made of biotinylated PEG(2000)-DSPE are loaded with a PDT drug. The aggregation of these micelles is induced by addition of streptavidin, which will pull the biotinylated micelles together forming large and rigid aggregates. The degree of aggregation can be controlled by manipulating parameters such as streptavidin:biotin ratios, reaction time, temperature, and degree of mixing and may be adjusted by those skilled in the art based on the disclosure herein without resort to undue experimentation. This will result in a dispersed distribution of micellar aggregates which are large and rigid due to streptavidin:biotin binding and non-aggregated micelle aggregates which are small and less rigid.

In another embodiment, a liposome or polymersome loaded with PDT drug (about 40 nm to about 200 nm in size) are fabricated using different lipid combinations. One formulation comprises lipids with different melting temperature ($T_m$). Liposomes made of higher $T_m$ lipids are more rigid while liposomes made of lower $T_m$ lipids are less rigid and can more easily be extruded to smaller size liposomes. By mixing desired proportions of these larger high $T_m$ lipid liposomes and smaller low $T_m$ lipid extruded liposomes, it is possible to achieve a distribution of liposomes with different sizes and rigidity.

Some examples of rigidity-size ratios are shown in Table 3 and 4.

In one embodiment, small metallic nanoparticles such as Fe or Au nanoparticles, nanocrystals, or q-dots (diameter of about 10 nm) are conjugated or coated with the drug onto their surfaces. These rigid nanoparticles have various sizes and size distributions. They can be selectively taken up by diseased tissue.

In one embodiment, rigid polymeric nanoparticles of various sizes (e.g. PLGA nanoparticles made by emulsion and solvent evaporation procedures and having a diameter of greater than 80 nm) are selectively taken up by diseased tissue.

The aforementioned nanoparticle formulations can be delivered via intravenous injection or minimally invasive intracoronary injection, infusion, coated balloon, or coated stent.

TABLE 3

Rigidity-size ratio of liposomes/micelles/polymeric nanoparticles (carbons:unsaturated)

| Size | Rigidity | | |
|---|---|---|---|
| | $T_g < 25°$ C. (flexible) | $25°$ C. $< T_g < 50°$ C. (intermediate) | $T_g > 50°$ C. (stiff) |
| <100 nm (small) | PEG-DSPE micelles, SoyPC-DSPG liposomes (2-8), DLPC 12:0 (−1), DMPC 14:0 (23), DOPC 18:1 (−20), DOPE 18:1 (−16), | DPPC 16:0 (41) | DSPC 18:0 (55), DMPE 14:00 (50), DPPE 16:0 (63) |
| 100-200 nm (intermediate) | SoyPC-DSPG liposomes (2-8), DLPC 12:0 (−1), DMPC 14:0 (23), DOPC 18:1 (−20), DOPE 18:1 (−16), | DPPC 16:0 (41) | DSPC 18:0 (55), DMPE 14:00 (50), DPPE 16:0 (63) |
| >200 nm (large) | Poly(ε-caprolactone) (−60), PEO (−67), Polyurethane (−50), LDPE (−20), PP (5) | PLGA (40-50), Nylon 6 (45), Nylon 66 (50), | PDLA (55, PLLA (65), PVP, PVA (85), PS (100), PAA (100), PET (65-105) |

TABLE 4

Rigidity-size ratio of polymeric nanoparticles based on elastic modulus

| Size | Rigidity | | |
|---|---|---|---|
| | E < 100 MPa (flexible) | 100 MPa < E < 1000 MPa (intermediate) | E > 1000 MPa (stiff) |
| <200 nm (small) | Calcium-alginate (made via microfluidics focusing), Chitosan, Hyaluronic acid | PCL-PEO blend | Metallic quantum dots (eg. CdSe, ZnSe), PLGA (50:50), poly(2-sulfobutyl-vinylalcohol)-g-PLGA, PLGA (50:50):tetronic blend, PLLA-b-PEO |
| >200 nm (large) | Polyurethane or polyurethane-urea (10-100) | LDPE (172-283), Polyurethane (100-500), R-PHB (1360) | PP (1170-1720), PS (2280-3280), Polycarbonate (2380), PLLA (2700), PDLA (1400), DL-PLGA (85:15; 75:25; 65:35; 50:50) (1400-2800) |

Annexin V recognizes cells with phosphatidyl serine in outer leaflets of cell membranes. Phosphatidyl serine is normally sequestered in the inner leaflet of the cell membrane, but is moved to the outer leaflet in apoptotic cells such as foam cells, activated platelets, smooth muscle cells, and non-apoptotic, lipid loaded cells, all of which are found in plaque and rupture prone lesions.

In one embodiment drugs such as, but not limited to, fenofibrate, dexamethasone and other gluocosteroids, statins, Darapladib, anti-inflammatory drugs, LY-518674, FfY720 and photosensitizers are encapsulated in the above polymeric particles using single, double emulsion, spray dry or extrusion technologies. The surfaces of the particles are conjugated to Annexin V with or without spacers for optimal efficacy.

In one embodiment, softer particles such as micelles, worm shape micelles, liposomes, polymersomes, low $T_g$ polymeric nanoparticles and niosomes of diameter of about 10 nm to about 150 nm can be loaded with the aforementioned drug or drugs optionally with hydrophilic drug such as bisphosphonates and ApoAI peptides. The surface of the particles can have functional groups such as amine, carboxyl, sulfhydryl for attachment of Annexin V or Protein G.

In one embodiment, the aforementioned polymeric nanoparticle or soft particles such as micelles, liposomes, and polymersomes can be appropriately sized for desired luminal penetration depth. For example, micelles or SUV liposomes would be expected to penetrate deeper compared with polymeric nanoparticles thereby targeting different regions of the diseased tissue.

Pro-survival proteins or agents such as IGF1, bFGF, PDGF or TGF-β may be delivered via Annexin V-modified nanoparticles described above to target apoptotic smooth muscle cells. Prevention of thinning of fibrous cap via smooth muscle cell apoptosis may prevention of cap rupture.

The nanoparticles described above can be conjugated with technetium-99m labeled Annexin A5. This label will provide concurrent imaging and therapy capabilities for vulnerable plaque using techniques such as MultiSpect.

In one embodiment, dual specific surface modification may be used, for example, without limitation: i) modification with Annexin V, and ii) modification with sialoprotein or ICAM, VCAM specific ligands. Surface modification with sialoprotein or ICAM, VCAM specific ligands will enhance rention of the EC and SMC and trap particle at the wall. Surface modification with Annexin V will effect specific uptake into macrophages.

The aforementioned particles and formulations thereof can be combined with a viscosity modifier to increase residence time along the vessel wall and increase the time at which Annexin V can act.

The aforementioned particles or formulations can be applied to a double occlusion balloon for local and or regional delivery in either the peripheral or coronary vasculature.

In many cases, the formulations have been delivered by local injection to the site or by attachment of a targeting component to the surface of the PDT carrier.

In one embodiment is provided a formulation and a method for delivering a mixture of different PDT drugs with different UV or visible absorption. The PDT drugs or formulations thereof are delivered via a porous balloon or a double denuded balloon to the lumen side of arterial tissues.

In one embodiment is provided a formulation and a method for delivering at least two photosensitizers that can be activated at two different wavelengths. A short wavelength activated PCT in the blue or green light region can be used for 200 nm to 400 nm penetration into a diseased tissue and a long wavelength PDT in the red or infrared region can be concurrently administered for deeper treatment of the diseased tissue. For example, MV0633 that can be excited at 406 nm can be administered for 200 nm to 400 nm deep penetration and treatment and a naphthalocyanine sensitizer that is excited at 750 nm with no significant excitation at the lesser wavelength can be concurrently administered for deeper penetration and treatment.

Another advantage of dual PDT formulations would be to allow a higher drug concentration at the surface and therefore use of a lower light dose to activate the drug to minimize tissue heat effects. The higher drug concentration may act as a "sun block" and prevent deeper tissue penetration by that specific wavelength PDT drug, which could be overcome by using a PDT with another absorption wavelength for deeper tissue penetration.

Alternatively, the second drug could be a different type of drug such as, without limitation, an anti-proliferative, anti-inflammatory, anti-thrombotic, pro-healing or pro-ECM deposition drug.

The drugs could be co-formulated into one formulation such as micelles, liposomes, nanoparticles, or nanoconjugates, etc. Alternatively, the formulation could be a mixture of two different particles, containing different drugs, but otherwise having the same carrier such as a liposome. The mixture can be of any desired ratio. Additionally the two drugs can be in two different formulations. An example is the above-referenced MV0633, which could be formulated in a liposome and co-delivered with naphthalocyanine in a micelle formulation. The formulations may be mixed and delivered simultaneously or they may be delivered in separate infusions from the delivery device.

In one embodiment, these dual agents are loaded into the same multicomponent micelles to provide distinct regions and release kinetics of each agent. Multicomponent micelles can be formed by combinations of hydrophilic and hydrophobic blocks in tri-block copolymers of low molecular weight. One example of tri-block star copolymer is PEO-PEE-PMCL.

Alternatively dual drugs can be loaded into biphasic or core-shell biodegradable nanoparticles. These nanoparticles can provide distinct release kinetics of the drugs as desired.

In one embodiment, one nanoparticle formulation and delivery medium with one drug encapsulated in the formulation is combined with a second drug, wherein the second drug is in solution.

The above multiple-drug formulations can be designed to release their loads on demand by application of a trigger such as, without limitation, heat, pH, light of specific wavelength or ligand/receptor interactions.

What is claimed:

1. A method of treating vulnerable plaque in a patient in need thereof, comprising:
    administering to the site of a vulnerable plaque, having a fibrous cap and an interior core, a first plurality of nanoparticles comprising a first PDT drug having an excitation wavelength in the blue-green region of the electromagnetic spectrum wherein the first plurality of nanoparticles either affix to the surface of the fibrous cap or penetrate only into the fibrous cap;
    concurrently administering to the site of the vulnerable plaque a second plurality of nanoparticles comprising a second PDT drug having an excitation wavelength in the red region of the electromagnetic spectrum wherein the nanoparticles are capable of penetrating into the interior of the plaque;
    exposing the vulnerable plaque site to either blue-green or red light; and, subsequently,
    exposing the vulnerable plaque site to light of the other excitation wavelength;
    wherein the second plurality of nanoparticles are negatively charged and include ceramide on their surfaces.

2. The method of claim 1, wherein the first and second plurality of nanoparticles are independently selected from the group consisting of micelles, liposomes, niosomes, polymersomes, polymeric nanoparticles, nanoconjugates and any combination thereof.

3. The method of claim 2, wherein the first plurality of nanoparticles, the second plurality of nanoparticles or the first and the second plurality of nanoparticles comprise a low molecular weight tri-block copolymer having hydrophilic and hydrophobic blocks.

4. The method of claim 3, wherein the tri-block copolymer is PEO-PEE-PMCL.

5. The method of claim 1, wherein the first plurality of nanoparticles, the second plurality of nanoparticles or the first and the second plurality of nanoparticles further comprise one or more non-PDT drugs.

6. The method of claim 5, wherein the non-PDT drug(s) is/are independently selected from the group consisting of an anti-proliferative drug, an anti-inflammatory drug, an anti-thrombotic drug, a pro-healing drug, and a pro-ECM deposition drug.

7. The method of claim 5, wherein the non-PDT drug(s) is/are independently selected from the group consisting of fenofibrate, glucosteroid, dexamethasone, a statin, Darapladib, LY 518674 and FTY 720.

8. The method of claim 5, wherein at least one non-PDT drug is hydrophilic.

9. The method of claim 8, wherein the hydrophilic drug is selected from the group consisting of bisphosphonate and ApoA1.

10. The method of claim 5, wherein the non-PDT drug(s) is/are a pro-survival protein or an agent selected from the group consisting of IGF-1, bFGF, PDGF, and TGF-$\beta$.

11. The method of claim 1, wherein administering the plurality of nanoparticles to the site of the vulnerable plaque comprises local injection at the site of the vulnerable plaque or infusion into the site of the vulnerable plaque from a delivery device.

12. The method of claim 11, wherein the delivery device comprises a balloon, porous balloon or double denuded balloon which is infused or coated with the nanoparticles.

13. The method of claim 2, where the first and second plurality of nanoparticles comprise a natural, semi-synthetic or synthetic biocompatible, biodegradable polymer.

14. The method of claim 13, wherein the biocompatible, biodegradable polymer is selected from the group consisting of dextran and copolymers thereof, alginate, cellulose, hyaluronan, chitosan, collagen, elastin, albumin, gelatin, PVP, PEG, PLGA, L-PLGA, PLGA-PEG, PCL, polyanhydrides, PEA, P(LLA-GA-CL), P(LA-GA-CL), P(LLA-CL), and polyacrylic acid.

15. The method of claim 1, wherein the surface of the nanoparticle comprises Annexin V or Protein G.

16. The method of claim 15, wherein the Annexin V is labeled with technetium-99m.

17. The method of claim 1, wherein the surface of the nanoparticles is modified using a substance selected from the group consisting of sialoprotein, ICAM specific ligand and VCAM specific ligands.

\* \* \* \* \*